US009265898B2

(12) United States Patent
Rajan et al.

(10) Patent No.: US 9,265,898 B2
(45) Date of Patent: Feb. 23, 2016

(54) APPLICATOR FOR OROPHARYNGEAL ANESTHETIC

(75) Inventors: Govind R. C. Rajan, Ballwin, MO (US); Marshall T. Denton, Salt Lake City, UT (US); Perry W. Croll, Salt Lake City, UT (US); Mark A. Christensen, Salt Lake City, UT (US); Timothy R. Wolfe, Salt Lake City, UT (US); J. Michael Brown, Salt Lake City, UT (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 254 days.

(21) Appl. No.: 12/733,490

(22) PCT Filed: Sep. 12, 2008

(86) PCT No.: PCT/US2008/010635
§ 371 (c)(1),
(2), (4) Date: Mar. 3, 2010

(87) PCT Pub. No.: WO2009/035646
PCT Pub. Date: Mar. 19, 2009

(65) Prior Publication Data
US 2010/0179511 A1 Jul. 15, 2010

Related U.S. Application Data

(60) Provisional application No. 60/971,820, filed on Sep. 12, 2007.

(51) Int. Cl.
*A61M 11/00* (2006.01)
*A61M 16/04* (2006.01)
*A61M 35/00* (2006.01)

(52) U.S. Cl.
CPC .............. *A61M 11/00* (2013.01); *A61M 11/007* (2014.02); *A61M 16/0488* (2013.01); *A61M 35/003* (2013.01)

(58) Field of Classification Search
CPC . A61M 16/0488; A61M 16/04; A61M 11/06; A61M 16/0409; A61M 16/0493; A61M 16/0495; A61M 2210/0656; A61M 11/00; A61M 11/007; A61M 35/003; A61B 1/267
USPC ......................................................... 600/187
See application file for complete search history.

(56) References Cited

U.S. PATENT DOCUMENTS 4,672,960 A 6/1987 Frankel
4,793,327 A 12/1988 Frankel
(Continued)

FOREIGN PATENT DOCUMENTS

WO WO 94-22422 A1 10/1994
WO WO 96-29066 A1 9/1996
(Continued)

OTHER PUBLICATIONS

PCT International Preliminary Report on Patentability, PCT/US2008/010635, dated Mar. 16, 2010.
PCT International Search Report, PCT/US2008/010635, dated Feb. 23, 2009.
(Continued)

*Primary Examiner* — Emily Schmidt
*Assistant Examiner* — Lauren M Peng
(74) *Attorney, Agent, or Firm* — TraskBritt, P.C.

(57) ABSTRACT

An anesthetic dispensing device (100) particularly adapted to apply anesthetic agent to the oral cavity and upper tracheal area of a medical patient prior to intubation of such patient. An exemplary dispenser (100) includes a handle (110) operably connected to a retractor (112) that carries an anesthetic dispensing device (104). A currently preferred dispensing device (104) includes a fluid-dispersing nozzle (118) in fluid communication with a syringe (116). Sometimes, an optical device (164) is coupled to the dispenser (100) to permit direct visualization of the application of anesthetic agent.

18 Claims, 11 Drawing Sheets

(56) References Cited

U.S. PATENT DOCUMENTS

| | | | |
|---|---|---|---|
| 4,825,858 A | | 5/1989 | Frankel |
| 5,112,297 A | * | 5/1992 | Stalcup et al. ............... 604/1 |
| 5,203,320 A | * | 4/1993 | Augustine ............... 600/187 |
| 5,431,152 A | | 7/1995 | Flam |
| 5,589,156 A | | 12/1996 | Henry |
| 5,593,661 A | | 1/1997 | Henry |
| 5,607,386 A | | 3/1997 | Flam |
| 5,679,325 A | * | 10/1997 | Henry ............... 424/45 |
| 5,791,341 A | | 8/1998 | Bullard |
| 5,858,331 A | | 1/1999 | Henry |
| 6,053,166 A | | 4/2000 | Gomez |
| 6,171,283 B1 | * | 1/2001 | Perez et al. ............... 604/192 |
| 6,698,429 B2 | | 3/2004 | Croll et al. |
| 2006/0247497 A1 | | 11/2006 | Gardner |

FOREIGN PATENT DOCUMENTS

| | | |
|---|---|---|
| WO | WO 99-39762 A1 | 8/1999 |
| WO | WO 2006-118984 A2 | 11/2006 |
| WO | WO 2009/035646 A1 | 3/2009 |

OTHER PUBLICATIONS

U.S. Appl. No. 12/586,098, filed Sep. 17, 2009 Rajan et al. Temporary Pharyngeal Airway.

U.S. Appl. No. 12/450,123, filed Sep. 11, 2009 Denton et al. Pressure Control for Catheter Drain Tubing.

U.S. Appl. No. 12/450,084, filed Sep. 10, 2009 Cheatham et al. Temporary Surgical Closure for a Body Cavity.

U.S. Appl. No. 11/219,319, filed Sep. 1, 2005 Christensen et al. Apparatus for Monitoring Intra-Abdominal Pressure.

U.S. Appl. No. 11/825,215, filed Jul. 3, 2007 Christensen et al. Apparatus for Monitoring Intra-Abdominal Pressure.

U.S. Appl. No. 10/737,656, filed Dec. 16, 2003 Denton et al. Vial Multi-Access Adapter.

U.S. Appl. No. 11/665,133, filed Apr. 11, 2007 Christensen et al. Intra-Abdominal Pressure Monitoring Device and Method.

U.S. Appl. No. 12/583,823, filed Aug. 26, 2009 Christensen et al. Medical Valve and Method to Monitor Intra-Abdominal Pressure.

U.S. Appl. No. 61/277,868, filed Sep. 30, 2009 Croll et al. Miniature Fluid Atomizer.

* cited by examiner

APPLICATOR FOR OROPHARYNGEAL ANESTHETIC

CROSS-REFERENCE TO RELATED APPLICATION

This application claims the benefit under 35 U.S.C. §119 (e) of U.S. Provisional Patent Application Ser. No. 60/971, 820, filed Sep. 12, 2007, for "APPLICATOR FOR OROPHARYNGEAL ANESTHETIC", the entire contents of which are incorporated herein by this reference.

TECHNICAL FIELD

The invention relates to devices (and associated methods) adapted to apply fluid to interior portions of a medical patient. In particular, certain embodiments are adapted to apply anesthetizing agent to portions of a conscious patient, typically extending from the oral cavity to the proximal trachea.

BACKGROUND OF THE INVENTION

Endotracheal intubation procedures are performed on certain medical patients. For example, a tube providing an airway may be introduced to assist the breathing of a patient having undergone certain kinds of trauma. The arcuate shape of a conventionally formed oral cavity and upper throat area of a human is known. Various devices are also known, having a cooperating arcuate shape, effective to assist in introducing a tube, or other medical device, through the mouth and into the throat of a patient.

One device effective to assist in introducing an endotracheal tube includes an arcuate-shaped laryngoscope blade. Such a blade typically is formed from metal, or a very stiff plastic-like material, and has a spatulate, axially curved shape formed to cooperate with the conventional shape of oral cavity structure. The curved spatula portion of the blade is used for retracting soft tissue and opening the patient's jaw and mouth to form a clear, open path through which a tube or instrument may be inserted. In general, a laryngoscope blade is transversely very stiff to permit its use as a retractor for soft and hard tissue, while resisting significant bending deflection of the curved portion of the blade. Significant bending deflection of the curved portion under a working load would undesirably place the proximal handle associated with the blade into a blocking position and thereby interfere with creating the desired clear passage through which installation of a tube may be visualized.

In those cases where the patient is unconscious, there is no patient gag reflex over which the medical practitioner must surmount to install a tube, or to insert some other medical device. Consequently, difficulty of an intubation procedure is greatly reduced, although not eliminated. However, there exist instances where the patient is awake, at least partially alert, desirably remains in such condition for a further period of time, and prompt intubation must be effected in spite of such facts. In such cases, the patient's own gag reflex can constitute a significant obstacle to intubation.

Awake endotracheal intubations are typically accomplished using a fiber optic guide, and require anesthetizing the oral cavity, oropharynx, tonsillar pillars, base of the tongue, supragottic region and vocal cords, and other deep pharyngeal structure, such as the deep posterior pharyngeal wall, pyriform fossa on either side of the larynx, vallecula, and on to the proximal trachea. Anesthetization typically starts with topical application of anesthetic fluid at the front of the oral cavity, and then progresses inward toward the tracheal-esophageal bifurcation area. Typically, an area will be numbed prior to moving on to the next deeper area. Unfortunately for the patient, each new area receiving anesthetic initially presents a new stimulated area to promote a gag reflex.

It is generally desirable to apply anesthetic agent in a substantially uniform coating to reduce waste and avoid over-, or under-, medication. Application of anesthetic topically by way of a transfer medium, such as a sponge, often produces a substantially non-uniform coating of agent on the patient's tissue, as well as physically imposing on non-anesthetized areas. Squirting anesthetic agent from the nozzle of a syringe, e.g., as a jet, is equally unsatisfactory, and also wasteful. Known misting nozzle arrangements are not satisfactory to apply anesthetic agent in all desired areas for an endotracheal intubation procedure.

BRIEF SUMMARY

The invention may be embodied to provide an anesthetic dispenser assembly including a holder having a handle operably connected to a proximal end of a retractor that is adapted for insertion into the mouth of a medical or veterinary patient to dispose the retractor's distal end in proximity to the patient's oropharyngeal tissue. The anesthetic dispenser assembly also includes a fluid dispensing device carried near the distal end of the retractor.

Sometimes, a fluid dispensing device can be embodied as a sponge. In other cases, a dispensing device includes a fluid dispensing nozzle. In certain cases, both a sponge and a nozzle may be included. A currently preferred fluid dispensing nozzle includes a fluid atomizer structured to impart spin to a fluid, about a spray axis passing through a discharge orifice, prior to ejecting that fluid from the orifice.

Desirably, the retractor is curved along a length axis effective to permit insertion of the retractor into the patient's mouth to dispose its distal end in approximate registration with the tracheal-esophageal bifurcation area of the patient. One currently preferred retractor has an axial bending stiffness, in a transverse direction, that is sufficiently large as to permit manipulation of the tongue of the patient effective to position the distal end at the bifurcation area, but that is too small to permit effective use of the dispenser as a laryngoscope blade. An exemplary retractor has an axial bending stiffness such that a load of about 20 pounds (9 kg) produces a tip deflection of at least ¾ inches (1.9 cm) during a tip-deflection test of a holder.

In certain embodiments, a syringe is operably connected to a fluid dispensing nozzle to permit dispensing a dose of fluid onto a patient's oropharyngeal tissue by depressing the plunger of the syringe. The syringe may be operably connected to the nozzle by way of a stretch of extension conduit. In certain cases, guide structure may be associated with the retractor and configured to hold a portion of the extension conduit. Desirably, the barrel of the syringe may be housed inside a portion of the handle.

Sometimes, the nozzle is oriented with respect to the retractor such that a spray axis of the nozzle is directed at an angle with respect to a local tangent axis near the distal end of the retractor. In certain embodiments, the nozzle may be fixed at an orientation with respect to the distal end of the retractor effective to permit dispensing fluid to an area prior to moving a portion of the retractor into contact with that area. Certain embodiments may include aiming structure configured to orient the nozzle for discharge directed at a surface disposed inside an axial curvature of the retractor. In certain embodiments, the nozzle may be manipulated, e.g., rotated or pivoted as desired, to orient its spray axis with respect to a local axis of the retractor.

In certain embodiments, the assembly is structured to permit loading the syringe as a decoupled element, then coupling the syringe to the nozzle and stowing the loaded syringe inside a portion of the handle. Desirably, structure of the handle is arranged to cooperate with structure associated with the syringe effective to permit dispensing a dose of fluid by depressing the plunger of the syringe with respect to the handle. Furthermore, sometimes an optical device may be coupled to the retractor effective to permit an operator to obtain direct visualization of fluid application to tissue inside the patient. In certain cases, it may be desirable for the optical device to be structurally coupled to the handle to permit an operator to effect one-handed application of anesthetic fluid to the patient's tissue while obtaining direct visualization of the fluid application.

In certain embodiments of the apparatus structured as described herein, the apparatus includes a holder having a handle operably connected to a proximal end of a retractor that is adapted for insertion into the mouth of a medical patient to dispose a distal end of the retractor in proximity to the patient's oropharyngeal tissue. Typically, the holder provides structure operable as a cavity in which to hold a syringe sized for reception within the cavity. Such an embodiment also includes a fluid dispenser, such as a fluid-dispersing nozzle disposed in fluid communication with the syringe and carried near the distal end of the retractor.

A method of using a dispensing assembly structured according to certain principles of the invention includes: loading a syringe with an anesthetic agent; coupling the syringe into fluid communication with an extension conduit to place the syringe in fluid communication with a dispensing nozzle; storing the syringe in a handle cavity of the dispensing assembly; inserting the distal end of the dispensing assembly through an awake patient's mouth to a first position along an arcuate conduit path extending toward the lungs of the patient; depressing the plunger of the syringe by an increment effective to issue a puff of anesthetic mist operably to wet and anesthetize a desired area; advancing the distal end to a new position further along the arcuate path; and repeating the depressing and advancing steps as required to effect satisfactory anesthetization of the patient. The method may also include obtaining direct visual confirmation of an application of a dose of an anesthetic fluid at an area not visible by an unaided observer located outside of the patient's mouth.

The device may be used to apply anesthetic fluid prior to endotracheal intubation of a conscious patient while reducing physical contact of the application device with un-anesthetized areas of the patient. It also allows for application of anesthetic as a more uniform coating to resist over-, or under-medicating the patient. It further provides a device with structure permitting direct observation of the application of the anesthetic agent.

BEST MODE OF THE INVENTION

Figure 1:
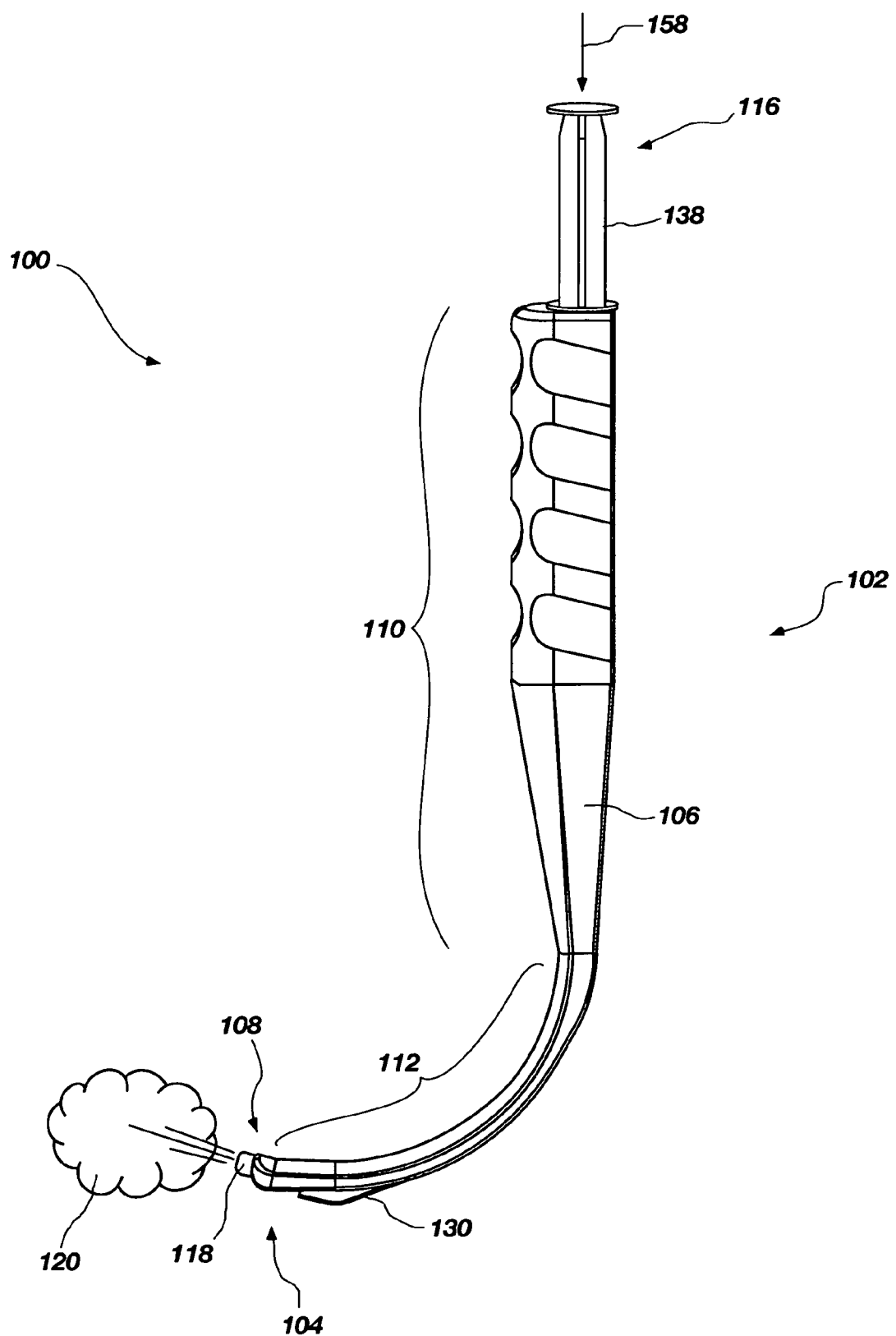
FIG. 1 is a side view of a currently preferred anesthetic applicator assembly that is constructed according to certain principles described herein.

Provided is an apparatus and method for applying anesthetic to facilitate certain medical procedures, such as endotracheal intubation of an awake patient. One currently preferred anesthetic dispensing device is indicated generally at 100 in FIG. 1. Device 100 includes a holder, generally 102, and a dispenser, generally 104. A workable holder 102 may be characterized as an elongate arm 106 having an anesthetic dispenser 104 carried at, or near, its distal tip 108. The holder 102 permits an operator or user (e.g., a health practitioner) to manipulate the dispenser 104 and apply anesthetic to selected interior portions of a patient's body.

Typically, the elongate arm 106 includes a handle part 110 and a retractor part 112. The handle 110 serves as a user interface for manipulating the device 100. A retractor 112 is operable to assist in manipulating parts of a patient's soft oropharyngeal tissue, such as the tongue. A handle 110 may be regarded as being operably connected to a proximal end of retractor 112. The connection location between respective components may be sharply defined by boundaries formed by distinct structure, or may be somewhat arbitrary, as illustrated. In practice, the handle 110 may be formed as a simple extension to the retractor 112.

Desirably, retractor 112 is relatively small in cross-section to minimize its intrusiveness inside the oral cavity. The illustrated device 100 may look superficially similar to a laryngoscope blade. However, in contrast to a laryngoscope blade, the axial bending stiffness of certain preferred retractors 112 is insufficient for such retractors to be effective as an intubation assist device. That is, certain embodiments have an axial bending stiffness, in a transverse direction, that is sufficiently large as to permit manipulation of the tongue of a patient effective to position the distal end 108 at the patient's tracheal bifurcation area, but that is too small to permit effective use of such embodiments as a laryngoscope blade.

A workable dispenser 104 is operable to apply topical local anesthetic agent to oropharyngeal tissues of a patient. In certain cases, a sponge-like device 114 (see, e.g., FIG. 8) may be used as a dispenser 104 carried on an applicator, such as device 100. However, it is currently preferred to apply the topical anesthetic agent by using a pressurized fluid source, such as a syringe, generally 116, that is loaded with a fluid, or fluidized, local anesthetic agent, in combination with an atomizing or misting nozzle 118 operable as the dispensing device 104.

Certain embodiments of an anesthetic dispensing device 100 may be adapted to administer topical anesthetic in a misted, or atomized, form. By atomized, it is meant that the discharged fluid is dispersed substantially as a mist or cloud 120 composed of very small droplets. It is believed that application of topical anesthetic in a misted form minimizes the amount of required anesthetic agent, produces a more uniform and better-dispersed coating of anesthetic agent, minimizes irritation to patient tissue during application of the anesthetic agent, and reduces likelihood of accidentally overdosing the patient, or causing patient lung-trauma resulting from aspiration of anesthetic fluid.

Details of a currently preferred holder 102 for an anesthetic dispensing device structured according to certain principles of the invention are illustrated in FIGS. 2-6. The illustrated holder 102 includes a handle portion 110 operably connected to a retractor portion 112. As illustrated, the handle portion 110 may advantageously include grip-enhancing texture 122, or other structural features, to assist a user of the device in manipulating the retractor portion 112 inside the oral cavity and throat of a patient.

The retractor 112 may be considered as resembling a spatula adapted to administer topical anesthetic to selected areas inside the oral cavity and upper throat of a medical patient. The illustrated retractor 112 may be characterized as having a somewhat broad and rounded cross-section taken through a width direction. While such spatulate shape is currently preferred, it is recognized that an operable retractor 112 may have a cross-section taken through its width that suggests other shapes, including substantially round, or even prismatic.

Desirably, a retractor 112 is adapted to manipulate certain oropharyngeal tissue. In general, the retractor 112 is configured for insertion into a patient's mouth, and may be used to press against the patient's tongue, or to manipulate other oropharyngeal tissue during an anesthetizing procedure. Therefore, the retractor 112 desirably includes one or more working surface that is adapted to avoid causing injury to tissue of the patient while contacting such tissue during use of the device. For example, the distal tip 108 is typically blunt, and corners that might come into contact with the patient's tissue are generally rounded. Generally, broad and rounded working surfaces are effective to move tissue out of the way sufficient to permit advancing the distal end 108 into the patient's throat without damaging the displaced tissue. The working surfaces, such as arcuate ramp 124, are typically smooth, to facilitate sliding the retractor with respect to oropharyngeal tissue.

The illustrated retractor 112 may be regarded as having an axially curved shape adapted to follow the arcuate path from the patient's mouth opening toward the lungs. Such arcuate path has an axis that may be defined by one or more mathematical formula. A tangent axis 126 (see FIGS. 4 and 6) may be defined at a local point along the retractor 112, such as near its distal tip 108. Desirably, the spray axis 128 of a discharge nozzle 118 (if present) is oriented at an advanced angle a with respect to the distal tangent axis 126, to aim the discharged anesthetic 120 more toward tissue on the inside of the arcuate path, or to accommodate a decreased radius of curvature of the arcuate path near the tracheal/esophageal bifurcation.

It is recognized that an atomized or misted discharge may form a 3-dimensional cloud 120 effective to coat the complete circumference of a location along the oropharyngeal pathway, even without preferential aiming of its discharge direction 128. However, it is currently preferred to aim the discharge direction 128 slightly toward tissue on the inside of the arcuate path. A workable advance angle a is believed to be between about zero degrees and about 45 degrees, with a currently preferred advance angle a being about 15 degrees.

While a workable holder 102 may be manufactured from a variety of materials appropriate for a medical device, including stainless steel, it is currently preferred to injection mold a holder 102 from a medical-grade plastic or plastic-like material, such as polypropylene, polycarbonate, polyvinylchloride, polyurethane, nylon, silicone, rubber, and the like. Such plastic-like material advantageously reduces risk of damage to a patient's teeth resulting from an inadvertent bite-down on the device during an anesthetizing procedure. Furthermore, it is currently preferred to dispose of an anesthetic dispensing assembly, such as assembly 100, subsequent to a single use, rather than incur the cost and overhead required to sterilize parts, such as the holder 102, for reuse. Therefore, the illustrated holder 102 is structured essentially as a simply moldable shell, to reduce the amount of its constituent material, and to reduce its cost of manufacture.

One currently preferred dispenser assembly 100 for a fluidized anesthetic agent is illustrated in FIG. 1, and includes a syringe 116 in combination with a dispensing nozzle 118. Advantageously, the dispensing nozzle 118 is an atomizing nozzle operable to apply the anesthetic as a mist, or cloud 120. Such atomizing nozzles 118 apply spin to a fluid (about an ejection axis 128) just prior to ejecting the fluid through a small diameter orifice. The spinning fluid experiences a pressure drop across the orifice, and is thereby effectively atomized. Radial spread of the ejected cloud 120 increases in correspondence with increases in the spin rate. Details of principles of operation and construction of certain operable atomizing nozzles that may be used as a dispensing nozzle 118 are disclosed in U.S. Pat. No. 6,698,429, titled "MEDICAL ATOMIZER", issued Mar. 2, 2004, to Perry W. Croll, et al., the entire disclosure of which is hereby incorporated as though set forth herein in its entirety.

As illustrated in FIG. 7, the dispensing nozzle 118 may be spaced apart from the syringe 116 by an extension conduit 130. Workable extension conduit 130 may be formed from medical grade tubing, such as ⅛ inch diameter clear plastic tubing. Such extension conduit 130 is typically transversely flexible, and may be formed into the illustrated curved shape. However, flexibility of an extension conduit 130 is not generally required. Sometimes, the extension conduit 130 may include a plastically malleable portion that is structured to help the conduit 130 maintain a deformed shape. In the currently preferred embodiment, the holder 102 itself is adapted to hold at least a distal portion of the extension conduit 130 in a desired shape and to orient the spray axis 128 of the dispensing nozzle 118. It is alternatively within contemplation to incorporate an extension conduit 130 as a constituent element of the holder 130, e.g., as a molded-in lumen.

With particular reference to FIGS. 2 and 6, one way to hold the distal portion of the extension conduit 130 in a desired shape and in registration with the retractor portion 112 of a holder 112 includes one or more guide structure 132. Illustrated guide structures 132 form a channel 134 in which to contain a portion of the conduit 130. The channel 134 may be sized to receive the conduit 130 in a press-fit arrangement. Adhesive may also (or alternatively) be used to resist separation of the conduit 130 from the channel 134. Of course, it should be realized that a guide channel 134 is not required. Alternative retention structure (such as spaced-apart prongs, rings, or any of a variety of grabbers) may be used to maintain the distal portion of the extension conduit 130 in sufficient registration with the holder 102. It is also within contemplation simply to bond the conduit 130 directly to a surface of the holder 102, such as by welding or through use of one or more adhesive agent. Also, an extension conduit 130 may be trapped between clamshell portions of an alternatively structured retractor 112.

It is currently preferred to maintain the distal portion of the extension conduit 130 substantially affixed to the retractor portion 112 of the holder 102 to provide a tidy and unobtrusive package for insertion into a patient's mouth. However, an intermediate portion of the extension conduit 130 (e.g., stretching between the proximal part of illustrated channel 134 toward the dispensing end of a syringe 116) desirably is free to move with respect to the handle 110. Such an arrangement facilitates attachment of the syringe 116 to the extension conduit 130 subsequent to loading the syringe 116 with anesthetizing agent. As illustrated, a convenient coupling, generally 136, between syringe 116 and conduit 130 may be formed through a luer-lock fitting.

Subsequent to coupling the syringe 116 to the extension conduit 130, a user may then conveniently store the syringe 116 in the handle 110 of a holder, such as the holder 110 illustrated in FIGS. 1-6. Desirably, the syringe 116 is held sufficiently to resist its axial motion with respect to the handle 110 to facilitate operation of the plunger 138. For examples, the syringe trigger 140 may be biased toward engagement with a proximal handle surface 142 (see FIG. 3), or the trigger 140 may be trapped inside a socket 145 (see FIG. 2) formed in the handle 110.

Figure 2:
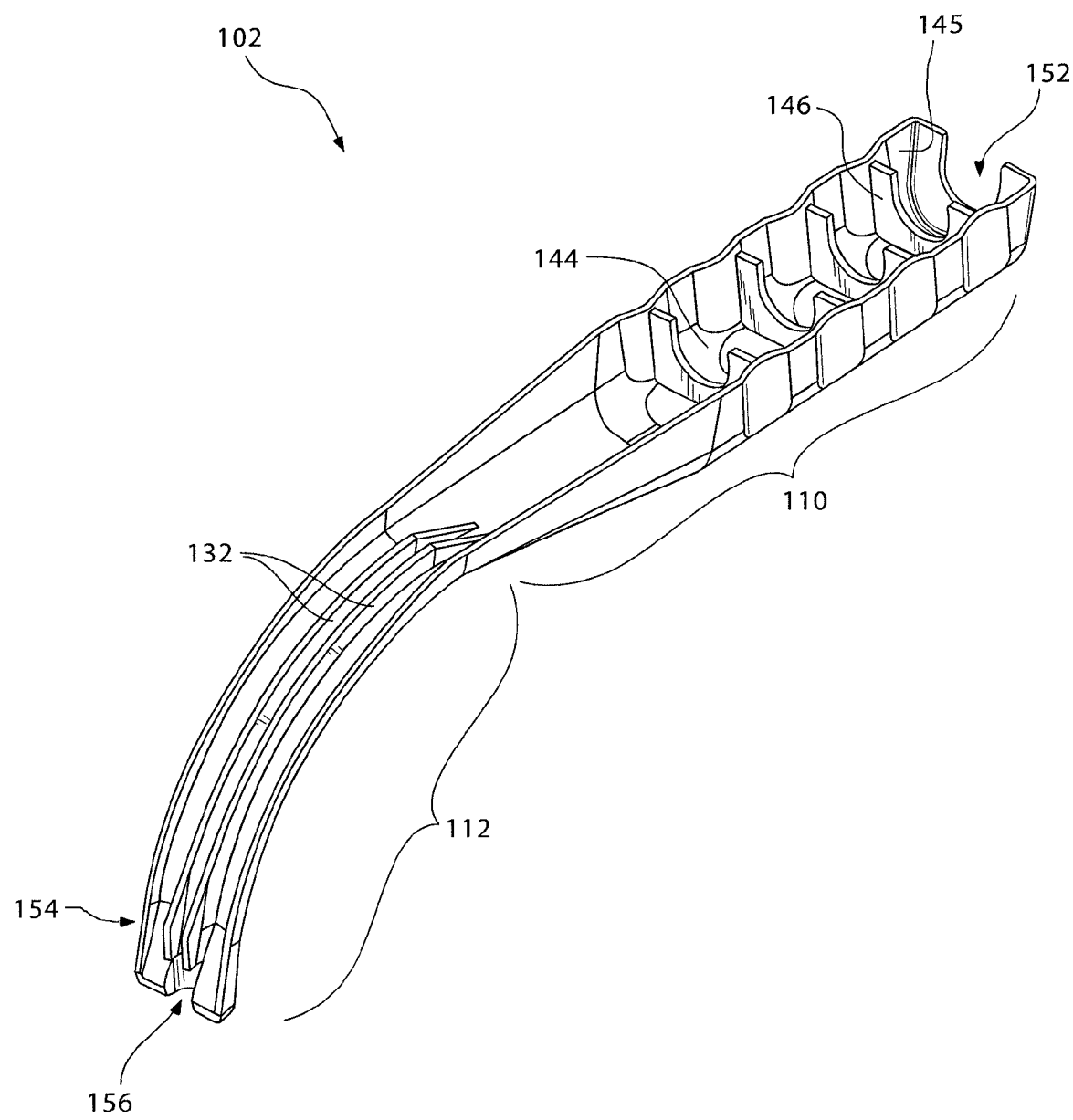
FIG. 2 is a top view in perspective of a holder portion of the device illustrated in FIG. 1.
Figure 3:
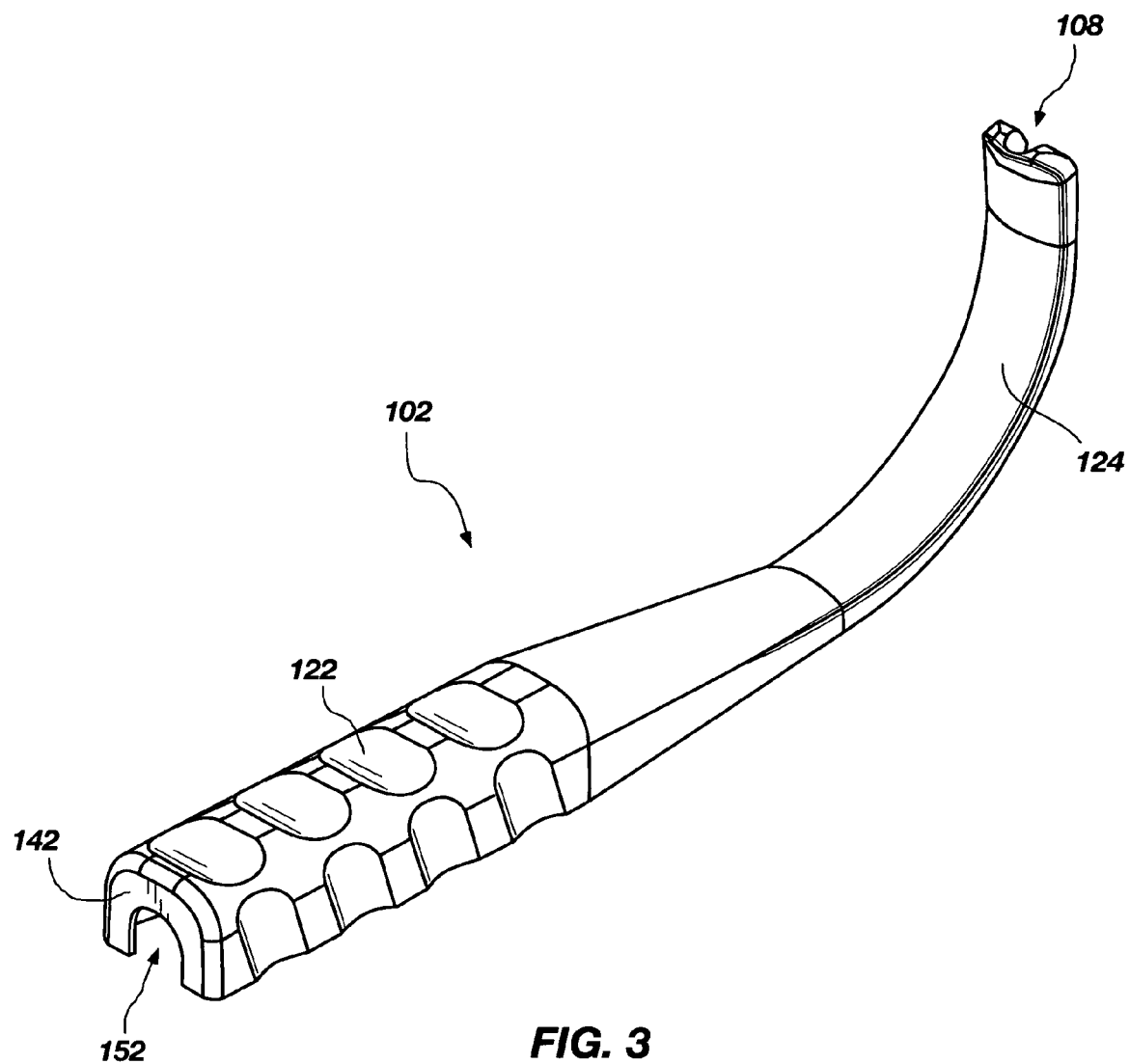
FIG. 3 is a bottom view in perspective of the device illustrated in FIG. 2.
Figure 6:
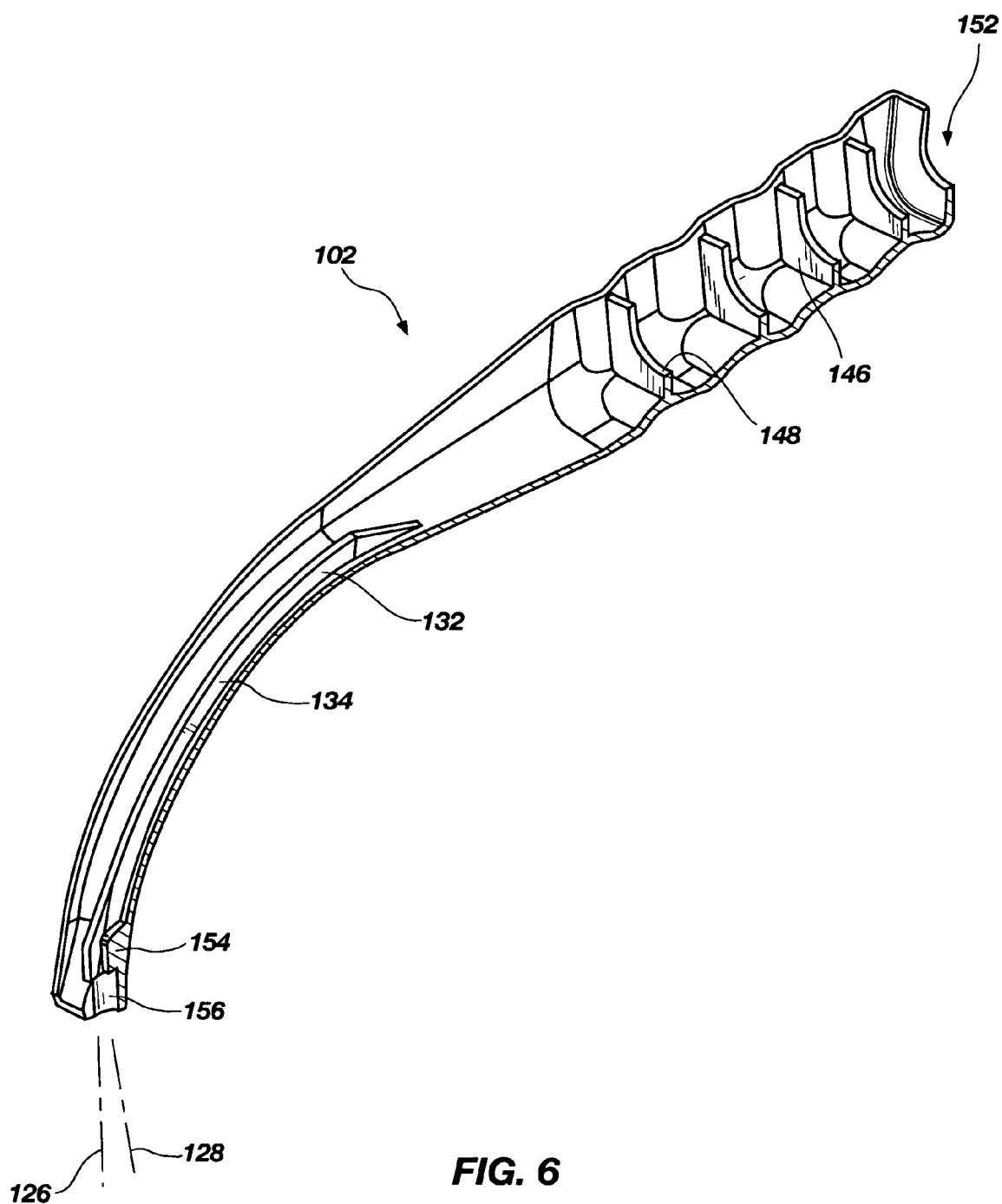
FIG. 6 is a top view in perspective of an axially oriented section of the device illustrated in FIG. 2.
Figure 7:
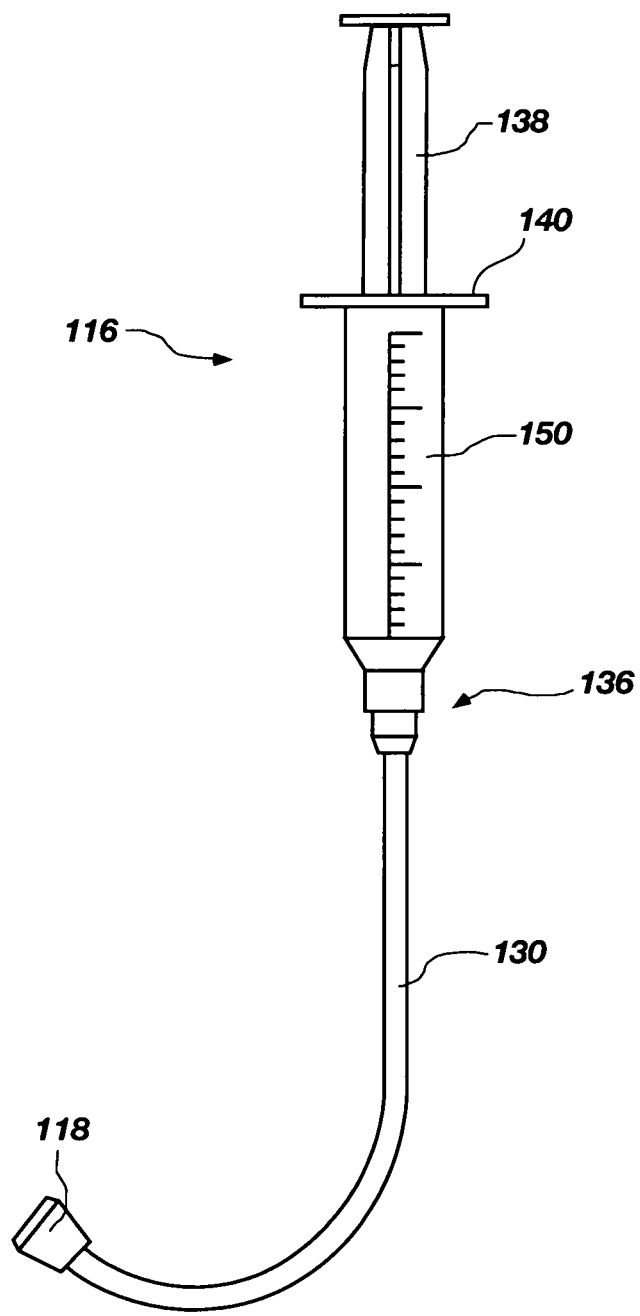
FIG. 7 is a side view of a workable anesthetic dispensing device in combination with a syringe, which constitutes part of the assembly illustrated in FIG. 1.

With particular reference to FIGS. 2 and 6, a syringe storage cavity 144 may be provided in a handle 110. The illustrated storage cavity 144 includes a plurality of ribs 146 adapted to form cradles 148 in which to receive the syringe barrel 150. In certain cases, one or more of such ribs can be configured to form a snap-fit effective to hold the syringe 116 in a stowed position. The syringe 116 may also, or alternatively, be held in place inside the handle 110 by a user's fingers, or palm. Tension in the extension conduit 130 may also be used to resist accidental separation of the syringe 116 from the storage cavity 144, and may also resist undesired axial motion of the syringe 116 with respect to the handle 110 to facilitate operation (depressing) of the plunger 138 when dispensing a dose of anesthetic agent. Opening 152 may be sized to receive barrel 150, or to accommodate plunger 138.

In another configuration, the syringe 116 may be attached to an extension conduit 130 having an extended length to permit operation of the syringe 116 outside of the handle 110 (e.g., for actuation of the syringe 116 by the user's free hand, or by another medical practitioner). However, it is currently preferred to store the syringe 116 inside the handle 110 to make essentially one-handed operation possible. In such case, the user's free hand can be used for other purposes (e.g., to manipulate the patient's head).

It is beneficial for the back of the syringe cavity to be open (as illustrated), or to otherwise to provide a window, to permit a user to observe the syringe 116 during a procedure. Such observation permits dispensing a desired incremental dose of anesthetic (as indicated in conventional fashion by the plunger's stopper and markings on the syringe barrel 150). A syringe 116 disposed outside the handle permits similar observation of an incrementally dispensed dose.

Figure 4:
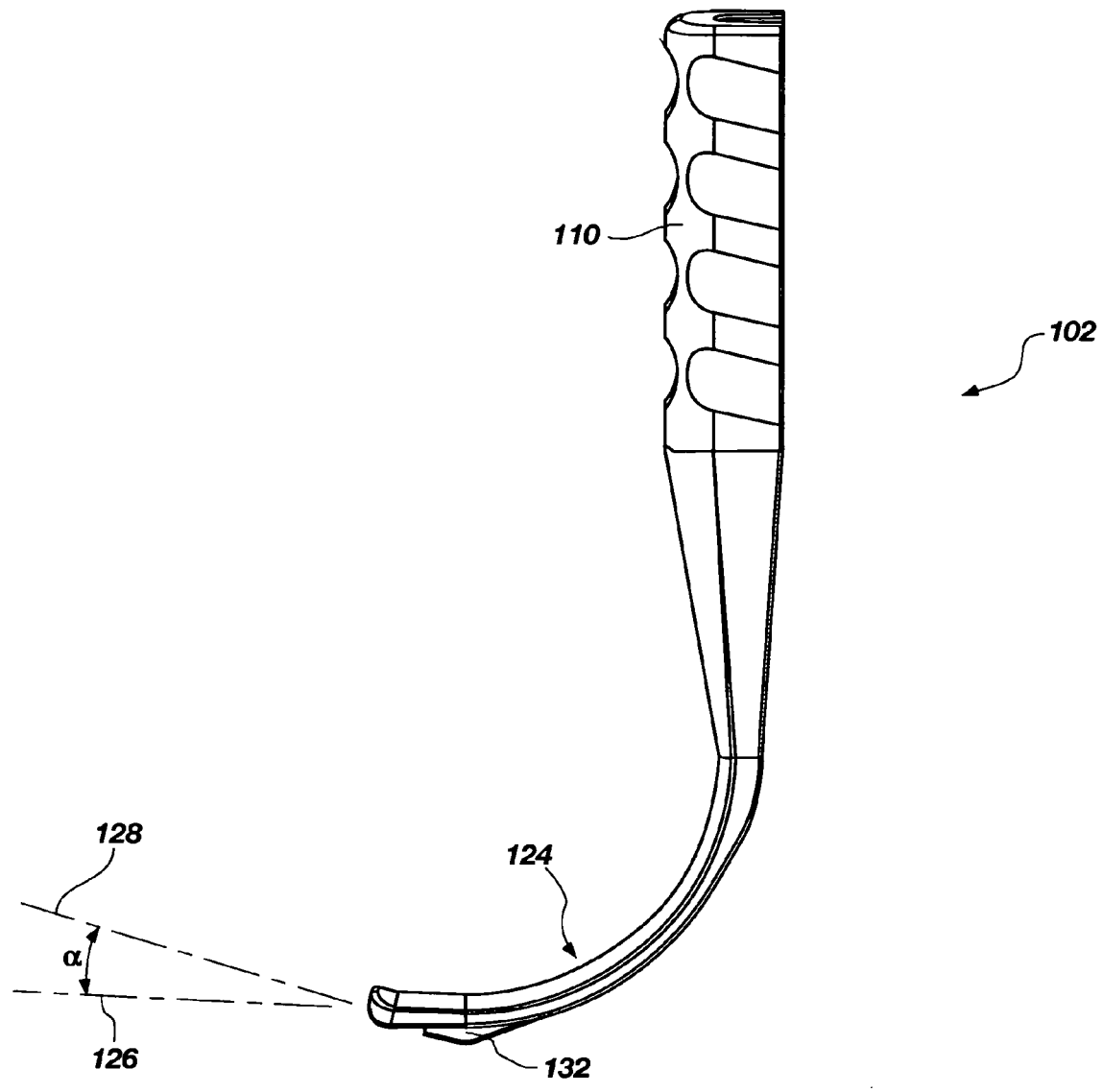
FIG. 4 is a side view of the device illustrated in FIG. 2.
Figure 5:
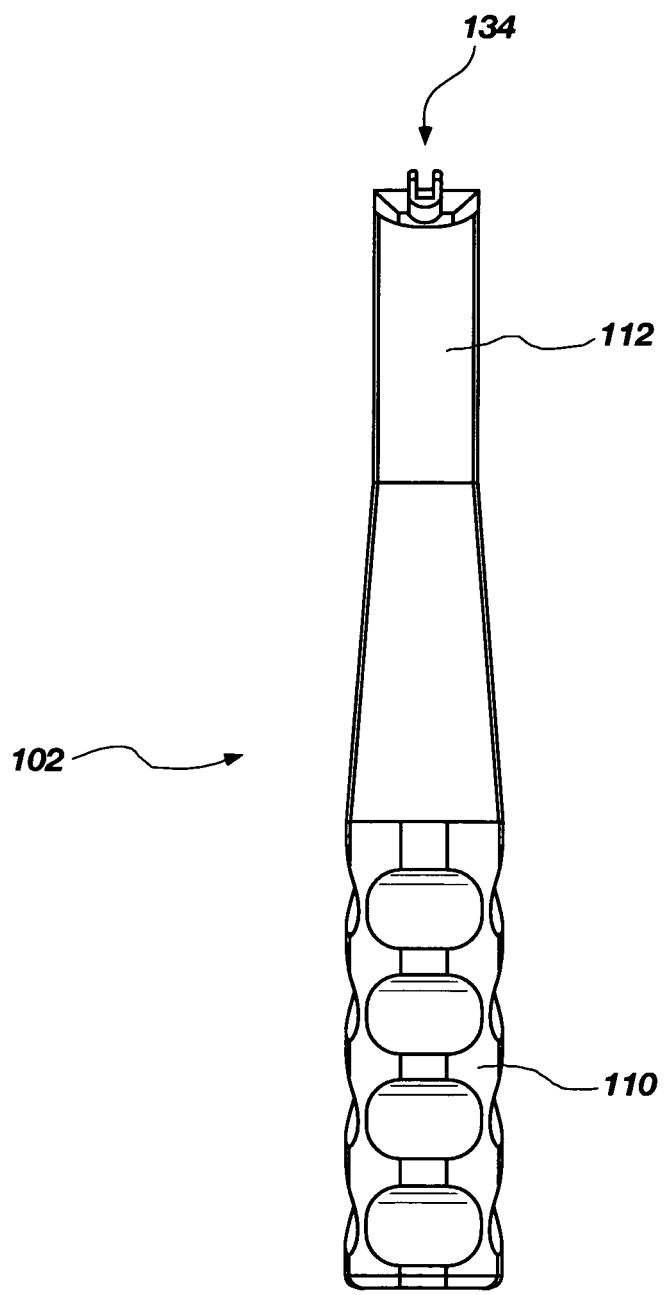
FIG. 5 is a bottom view of the device illustrated in FIG. 2.

Desirably, the retractor 112 is configured to provide an axially curved shape (e.g., in side-profile, such as illustrated in FIG. 4) adapted to cooperate with a patient's tongue and/or other oropharyngeal structure operably to permit its insertion through the mouth to dispose the distal dispensing tip 108 in approximate registration with the tracheal/esophageal intersection area. The retractor 112 may be formed in a variety of sizes and shapes to permit selection of a retractor 112 that cooperates with the size and shape of a given patient's oropharyngeal structure. One workable shape includes the illustrated substantially constant curvature that may be characterized as approximately forming a quadrant of an ovaloid, such as a circle or shallow ellipse, or a portion of a parabola, or other curve. The handle 110 is then operably connected to a portion of the retractor 112. One operable handle 110 projects proximally and substantially tangentially from its intersection with proximal structure of retractor 112, as illustrated in FIGS. 1-6.

As best illustrated in FIGS. 1 and 4, it is currently believed to be advantageous for the spray axis 128 of certain anesthetic dispensing devices to be nonlinear with, or nonparallel to, an imaginary and approximately tangent axis 126 extending from the distal end 108 of the retractor 112. In such configuration, structure at the distal tip 108 of the retractor 112 may be configured to optimize the tissue-manipulating "spatula", while the direction of spray discharge 128 may be optimized to promote uniform application of anesthetic agent over oropharyngeal tissue, especially, e.g., tracheal tissue near full-depth insertion of the retractor.

Of course, sufficiently uniform application of anesthetic agent over oropharyngeal tissue may also be promoted by optimizing a spray discharge. For example, the transverse diameter of an ejected cloud 120 of anesthetic agent may be increased by increasing the fluid spin prior to ejection. A cloud 120 of sufficiently large diameter inherently will tend to coat a full circumference of the patient's oropharyngeal conduit.

The angle a between the distal tangent axis 126 and spray axis 128 may be characterized as the spray angle. The illustrated spray angle a is regarded as being "advanced" in comparison to the illustrated distal tangent axis 126. It is currently believed that an optimal spray angle a may be selected from between about zero degrees and about 45 degrees, at least for a retractor structured as illustrated in FIGS. 1-6. Structure may be provided to orient the discharge direction of the nozzle, such as the aiming ramp 154 disposed near the distal tip 108 of the retractor 112 (see FIG. 6).

As best illustrated in FIGS. 2 and 6, the retractor 112 includes an optional nozzle cavity 156 sized to receive the dispensing nozzle 118 operably to permit dispensing an unimpeded spray pattern. A cavity 156 may also assist in resisting imparting injury to tissue from the nozzle 118. Of course, it is within contemplation simply to structure the nozzle 118 itself to avoid causing such injury.

Operation of one currently preferred embodiment (e.g., device 100 in FIG. 1) to dispense anesthetic agent may be effected by pressing the plunger 138 by the thumb of the user's manipulating hand, or a thumb, one or more finger(s), or the palm of the other hand. The user can rotate the retractor 112 side-to-side (e.g., about either a handle axis, or a distal tangent axis, or even some other axis), to ensure complete wetting coverage of tissue occurs. As illustrated, the spray axis 128 is desirably oriented at an advance angle a with respect to the tangent axis 126 to facilitate complete wetting of tissue disposed on the inside of the arcuate axial shape formed in the retractor body. Anesthetic is typically applied, then the distal tip 108 is inserted a bit further, and another dose of anesthetic is applied. Such process is repeated until the conscious patient is anesthetized sufficiently to undergo the intubation procedure. The applicator 100 may be withdrawn, and an intubation procedure can be started. In certain circumstances, intubation may be commenced prior to withdrawal of an anesthetic dispensing device.

In one method for anesthetizing an awake patient in preparation for intubation: first, the syringe 116 is loaded, typically in conventional manner, with a quantity of anesthetic. Second, the loaded syringe 116 is coupled in fluid communication with the extension conduit 130. A loaded syringe 116 may be conveniently stored in the handle 110 of a holder 102. Third, the distal end 108 of the retractor 112 is inserted through the conscious patient's mouth to a first position along the arcuate path toward the lungs. Fourth, the plunger 138 of the syringe 116 is depressed (as indicated by arrow 158 in FIG. 1) by an increment to issue a puff of anesthetic mist 120 operably to wet and anesthetize a desired area. It is within contemplation that an alternative anesthetic dispensing assembly may be structured to permit the spray angle a to be adjusted by pivoting or rotating the nozzle (even between retarded and advanced angles) by the medical practitioner while the retractor 112 is held substantially stationary. Fifth, the retractor 112 is advanced to a new position further along the arcuate path, and the fourth step is repeated. The fifth step may be repeated as required to effect satisfactory anesthetization of the patient. In certain cases, spraying anesthetic while retracting the base of the tongue anteriorly as the patient simultaneously takes a deep breath may yield best results.

Figure 8:
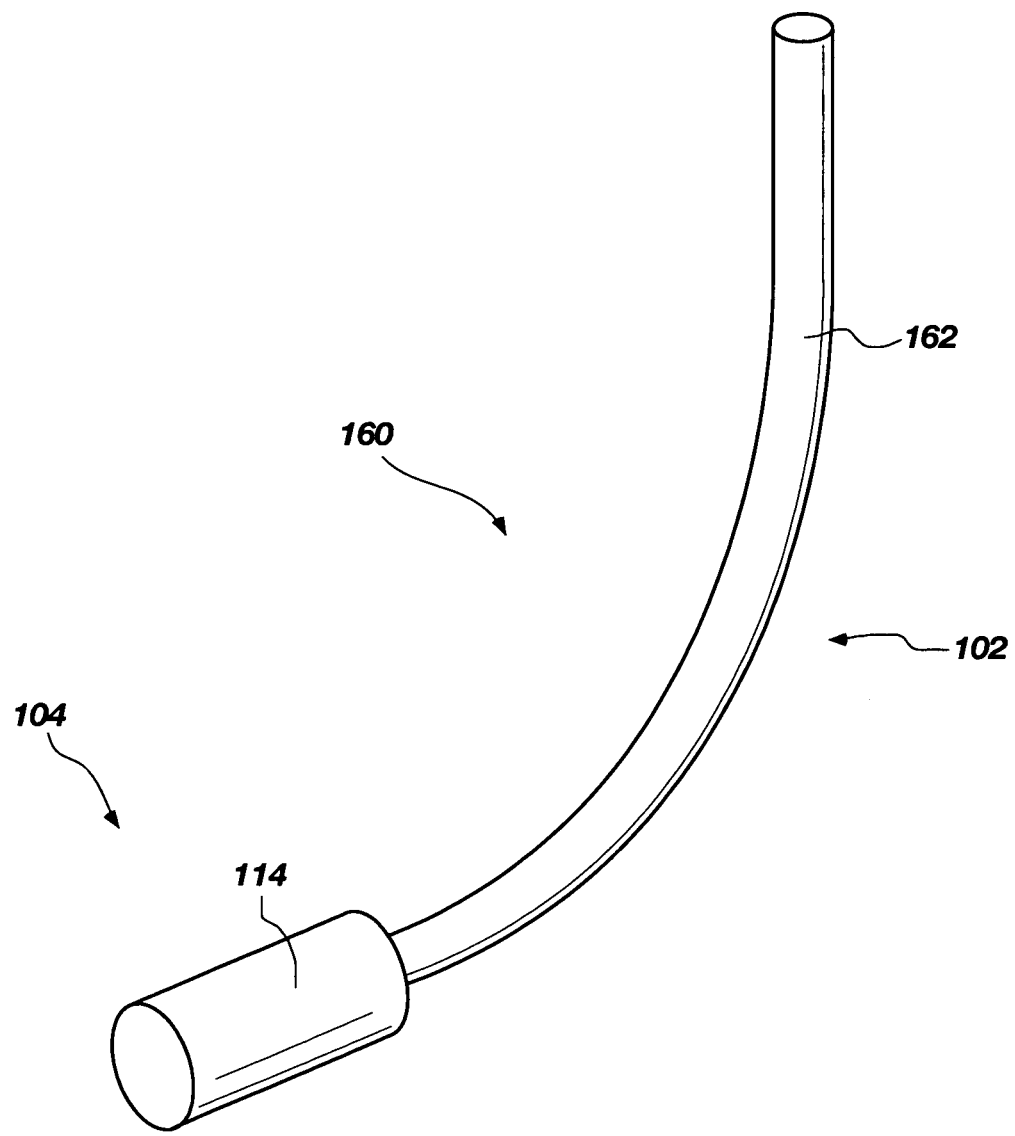
FIG. 8 is a side view in perspective of an alternative anesthetic applicator assembly that is constructed according to certain principles described herein.

Of course, anesthetization of at least portions of the oral cavity to begin an anesthetization procedure may alternatively be effected using a direct transfer device (e.g., a sponge 114, or cloth), as the dispenser for the anesthetizing agent. One operable alternative dispenser, generally 160, includes a sponge 114 carried at a distal end of a curved elongate arm 162, and is illustrated in FIG. 8. The axial curvature of the elongate arm 162 illustrated in FIG. 8 is similar to the axial curvature of the holder 102 illustrated in FIGS. 1-5. An operable elongate arm 162 to carry the sponge 114 can be manufactured from a relatively soft medical grade plastic, or plastic-like, material. The elongate arm 162 should provide sufficient transverse stiffness to permit pressing the sponge 114 against a surface of tissue to be anesthetized operably to transfer anesthetic agent to such surface.

A distal sponge 114, or other direct transfer device, may also be optionally included in a device having a spray nozzle anesthetic dispenser. As previously mentioned, a direct transfer device, such as sponge 114, may be carried at the distal tip 108 of an alternative embodiment of device 100. The direct transfer device 114 may be attached temporarily, or substantially permanently. An operable sponge 114 may be manufactured from any medically suitable material that can hold a quantity of fluid, and transfer that fluid to a surface upon pressing contact with that surface by the sponge material.

Figure 9:
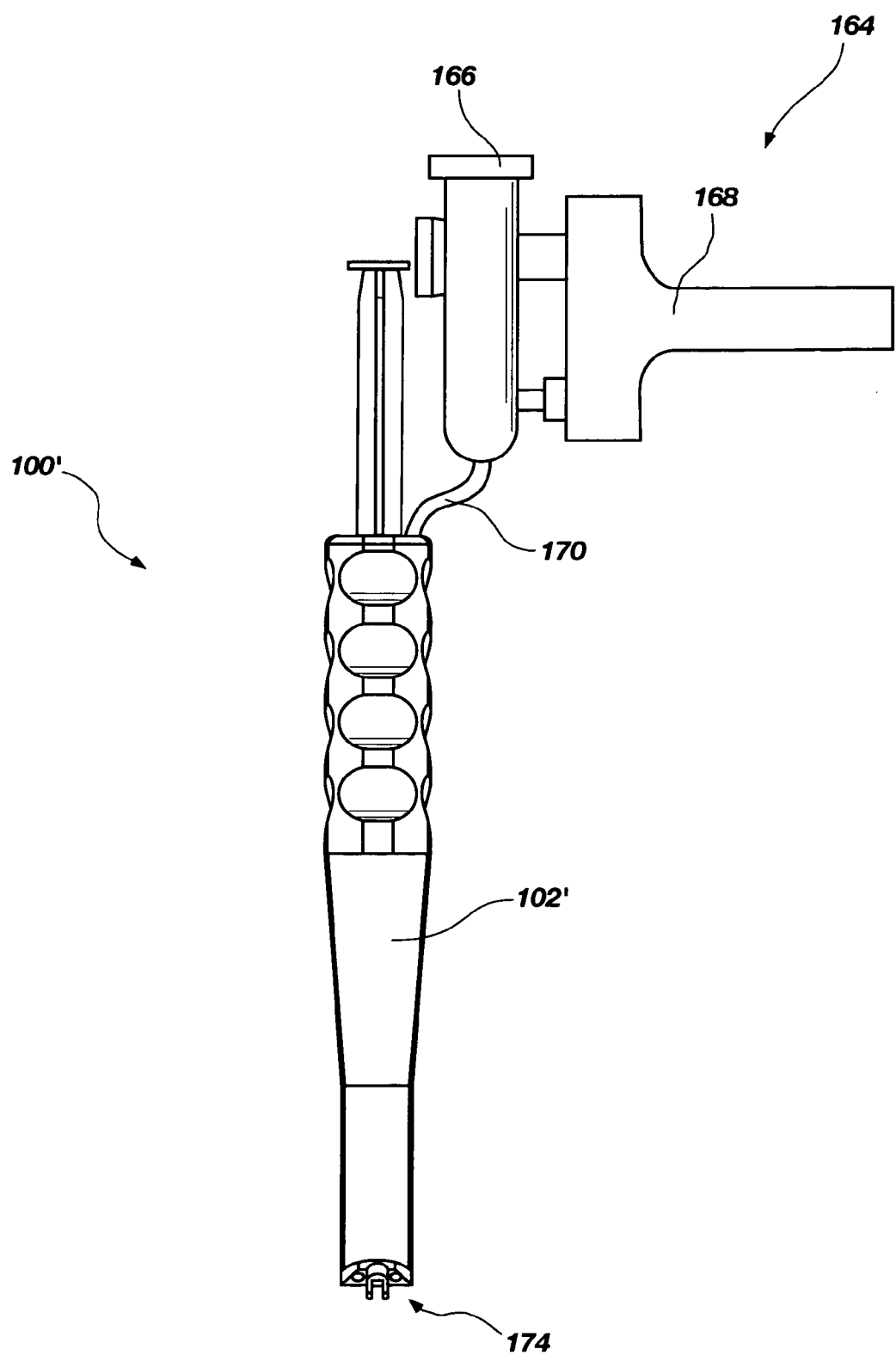
FIG. 9 is a bottom view of an alternatively structured anesthetic applicator that provides a user with direct visualization of anesthetic application.
Figure 11:
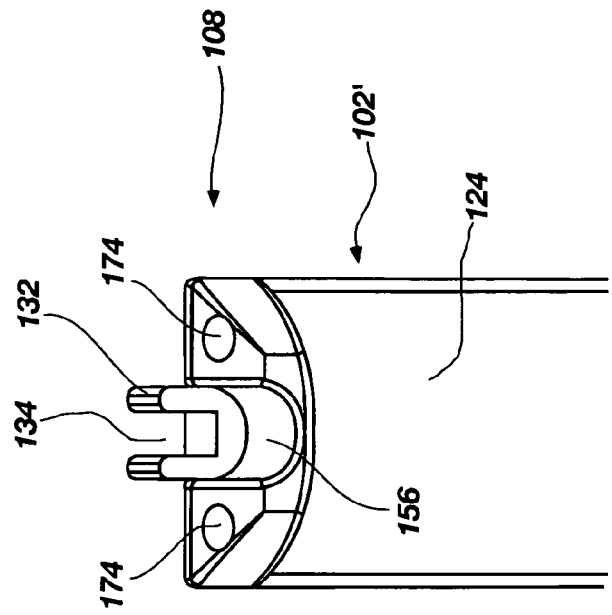
FIG. 11 is a top view of the distal tip portion of the handle illustrated in FIG. 10.
Figure 10:
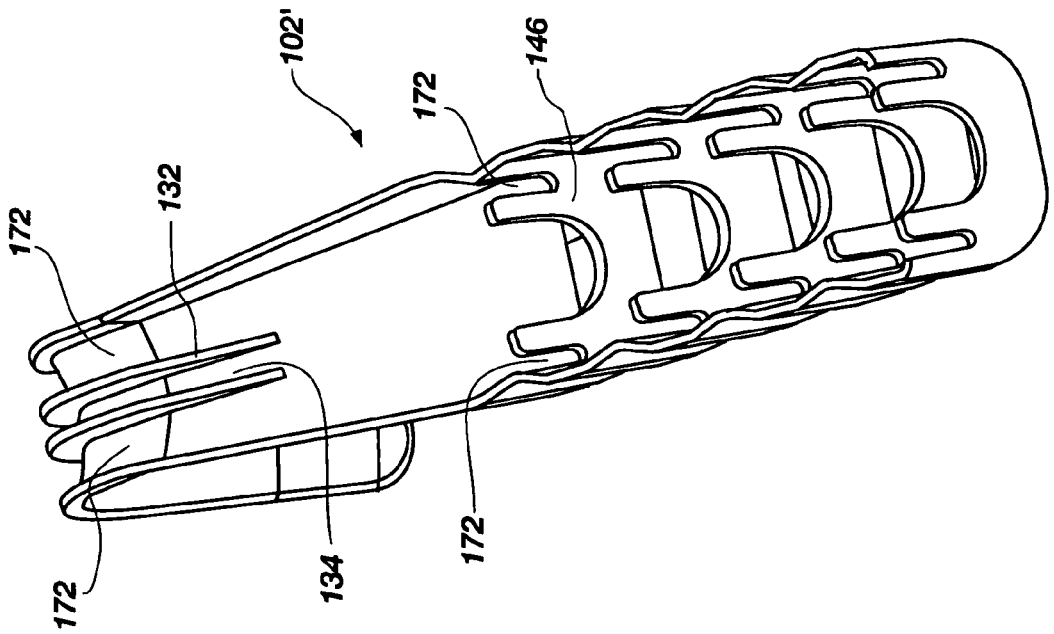
FIG. 10 is a perspective view from below of the proximal portion of a handle of the apparatus illustrated in FIG. 9.

With reference now to FIGS. 9-11, an alternative anesthetic applicator 100' that provides a user with direct visualization of the application of anesthetic agent will be described. Applicator 100' is substantially similar to applicator 100, but further includes an optical device, generally 164, capable of transferring the image of the application location to an eyepiece 166 for a user's visual input. A workable optical device 164 includes a Foley Airway Stylet (FAST), part No. 30505-10, available from Clarus Medical, LLC, having a place of business located at 1000 Boone Ave. N., Ste. 300, Minneapolis, Minn. 55427.

Illustrated optical device 164 includes a handle 168, inside of which a power supply and light source are disposed. It is within contemplation that the device 164 may include an extension cord to provide electrical power. A fiber optic cable 170 can be routed through the retractor 112' to distal tip 108. The illustrated holder 102' includes a pair of passageways 172 to optionally receive cable 170 on either side of the holder 102', to permit associating device 164 for use with holder 102' in either right-handed, or left-handed, operation by a user. A pair of apertures 174 is disposed at the end 108, one of which may be used to aim the distal end of cable 170 at the fluid application zone. Desirably, the retractor and distal portion of the handle are structured to resist damage to the cable 170 by a patient's teeth resulting from an inadvertent bite-down on the device during an anesthetizing procedure.

Device 164 may be associated with a holder 102' by way of attach structure that is not illustrated, but is believed to be within the grasp of one of ordinary skill in this art. For example, a tongue depressor-like extension that can be taped to the holder 102', and to which the device 164 may be taped, would be operable.

Figure 12:
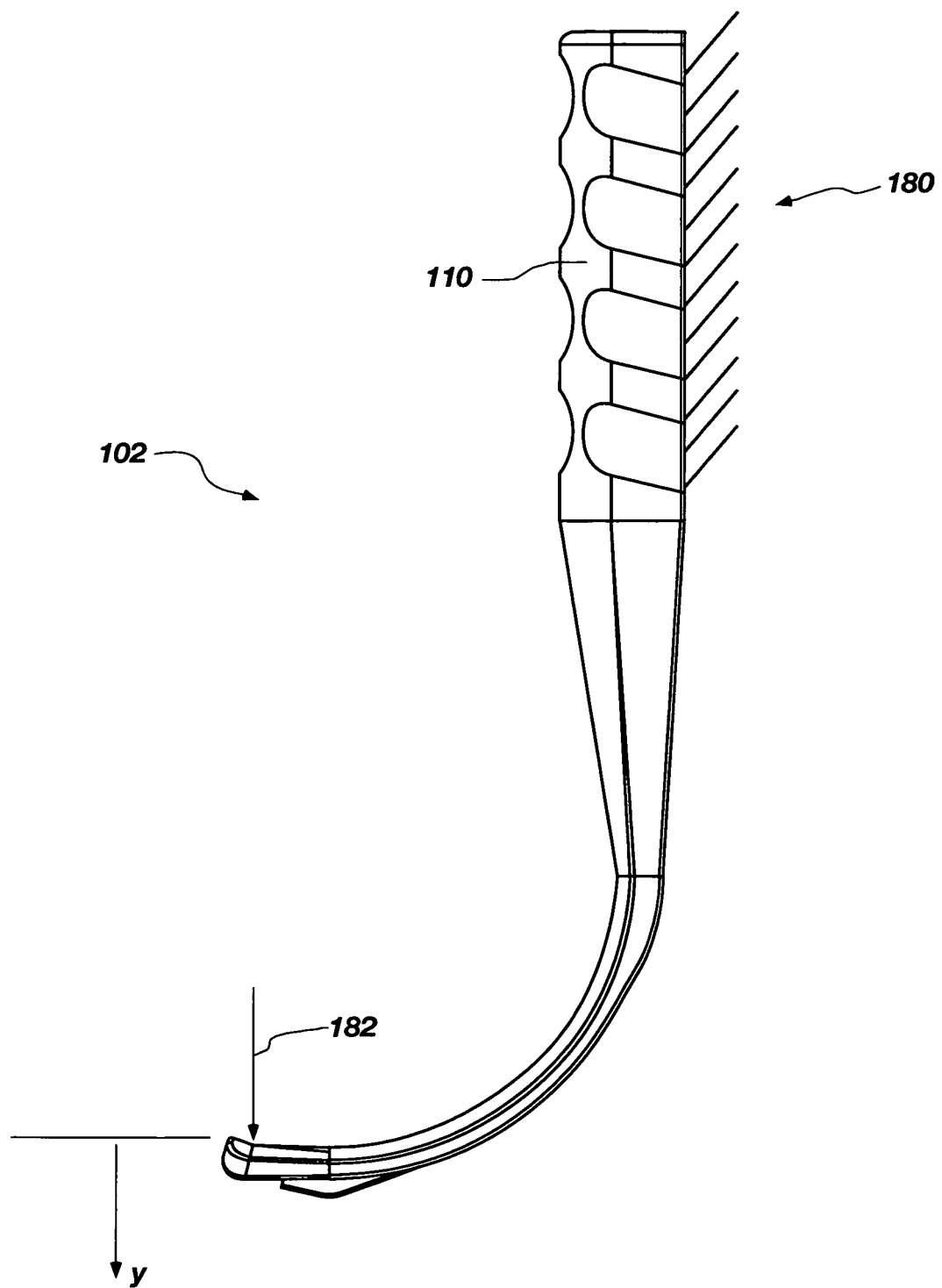
FIG. 12 is a side view illustrative of a test set-up to perform a tip-deflection test for a handle.

A tip-deflection test of a holder, such as holder 102, may be defined with reference to FIG. 12. A proximal portion of the holder, such as handle 110, is fixed, as indicated generally at 180, to resist its rotation and vertical displacement. A vertical load 182 is applied substantially at the end of retractor tip 108, and vertical deflection of the tip 108 is measured from an initial un-loaded position. The load required to deflect the tip 108 by various increments, and for three different conformations of holder, is shown in Tables 1-3.

With reference to data set forth in Tables 1-3, "Blue" represents data corresponding to a holder having the conformation illustrated in FIG. 12, and manufactured from polycarbonate. "Blue" data are representative of a holder having approximately the maximum desired transverse stiffness for certain preferred embodiments. "SLA" represents data corresponding to a holder having the conformation illustrated in FIG. 12, and manufactured with a rapid-prototyping stereolithic process from ABS. "SLA" data are representative of a holder having a transverse stiffness that is currently believed to be approximately the minimum for a holder to be useful as an anesthetic dispensing device structured according to certain principles of the invention. "Glide" represents data corresponding to a disposable plastic blade from the GVL Stat Cobalt single-use Glide-Scope, available from Verathane, having a place of business located at 20001 North Creek Parkway, Bothell, Wash. 98011 US. The latter component is the installation blade for a laryngoscope, and is believed to be at least representative of, if not actually, the most transversely flexible such blade available.

TABLE 1

| Blue | |
|---|---|
| Deflection Y (inch) | Load (pounds) |
| ¼ (0.6 cm) | 5.8 (2.6 kg) |
| ½ (1.27 cm) | 11.5 (5.2 kg) |
| ¾ (1.9 cm) | 17.8 (8.1 kg) |

TABLE 2

| SLA | |
|---|---|
| Deflection Y (inch) | Load (pounds) |
| ¼ (0.6 cm) | 0.5 (0.2 kg) |
| ½ (1.27 cm) | 1.7 (0.8 kg) |
| ¾ (1.9 cm) | 4.1 (1.9 kg) |

TABLE 3

Glide

| Deflection Y (inch) | Load (pounds) |
| --- | --- |
| ¼ (0.6 cm) | 16.6 (7.5 kg) |
| ½ (1.27 cm) | 26.9 (12 kg) |
| ¾ (1.9 cm) | 56.6 (26.7 kg) |

The transverse flexibility of the retractor 112 of a handle (e.g., 102, 102') operable in certain currently preferred embodiments sets such handle apart from an operable laryngoscope blade. With reference to the load data presented in Tables 1-3, it can be seen that the holder 102 of a currently preferred embodiment is distinguished over a laryngoscope blade (that is believed to be the most flexible available) by a factor of over 3-times load-carrying capability for a tip deflection of ¾ inch. That is, a holder 102 of a currently preferred embodiment may be characterized as being about three-times as flexible as the plastic laryngoscope blade believed to be the most flexible available. Therefore, certain currently preferred embodiments are even further distinguished over a conventional laryngoscope blade that is made from steel, which is much more transversely stiff than the plastic material used in the GVL Stat device.

What is claimed is:

1. An apparatus comprising:
a holder including a handle operably connected to a proximal end of a retractor that is adapted for insertion into the mouth of a medical patient to dispose a distal end of the retractor in proximity to oropharyngeal tissue, wherein the retractor is curved along a length axis effective to permit insertion of the retractor into the mouth to dispose the distal end in approximate registration with the tracheal-esophageal bifurcation area of the patient and further wherein the retractor has an axial bending stiffness, in a transverse direction, which axial bending stiffness is sufficiently large to permit moving the tongue of the medical patient effective to permit advancing the distal end of the retractor to the bifurcation area, but is too small to permit effective use of the apparatus as a laryngoscope blade, wherein the retractor has an axial bending stiffness such that a load of about 20 pounds (9 kg) produces a tip deflection of at least 0.75 inches (1.9 cm) during a tip-deflection test of a holder; and
a fluid dispenser carried near the retractor's distal end.

2. The apparatus of claim 1, wherein the fluid dispenser comprises a sponge.

3. The apparatus of claim 1, wherein the fluid dispenser comprises a fluid dispensing nozzle.

4. The apparatus of claim 3, wherein the nozzle comprises a fluid atomizer structured to impart spin to a fluid about a spray axis passing through a discharge orifice prior to ejecting the fluid from the orifice.

5. The apparatus of claim 3, further comprising a syringe operably connected to the nozzle to permit dispensing a dose of fluid by depressing a plunger of the syringe.

6. The apparatus of claim 5, wherein a barrel of the syringe may be housed inside a portion of the handle.

7. The apparatus of claim 5, wherein the apparatus is structured to permit loading the syringe as a decoupled element, then coupling the syringe to the nozzle and stowing the loaded syringe inside a portion of the handle.

8. The apparatus of claim 5, wherein structure of the handle is arranged to cooperate with structure associated with the syringe effective to permit dispensing a dose of fluid by depressing the plunger of the syringe with respect to the handle.

9. The apparatus of claim 3, wherein the nozzle is oriented with respect to the retractor such that a spray axis of the nozzle is directed at an angle to a tangent axis near the distal end of the retractor.

10. The apparatus of claim 3, wherein the nozzle is oriented with respect to the distal end of the retractor effective to permit dispensing fluid to an area prior to moving a portion of the retractor into contact with the area.

11. The apparatus of claim 3, the retractor further comprising an aiming structure configured to orient the nozzle for discharge directed at a surface disposed inside an axial curvature of the retractor.

12. The apparatus of claim 3, further comprising:
a syringe operably connected to the nozzle by way of a stretch of extension conduit to permit dispensing a dose of fluid by depressing a plunger of the syringe; and
a guide structure associated with the retractor and configured to hold a portion of the extension conduit.

13. The apparatus of claim 3, wherein the nozzle may be manipulated to orient its spray axis with respect to a local axis of the retractor.

14. The apparatus of claim 1, further comprising an optical device coupled to the retractor effective to permit an operator to obtain direct visualization of fluid application to tissue inside the patient.

15. The apparatus of claim 14, wherein the optical device is structurally coupled to the handle to permit the operator to effect one-handed application of fluid to the tissue while obtaining direct visualization of the fluid application.

16. The apparatus of claim 1, wherein the holder further comprises at least one rib configured to form a snap-fit effective to hold the syringe.

17. An apparatus comprising:
a holder including a handle operably connected to a proximal end of a retractor that is adapted for insertion into the mouth of a subject to dispose a distal end of the retractor in proximity to oropharyngeal tissue, wherein the retractor is curved along a length axis effective to permit insertion of the retractor into the mouth to dispose the distal end in approximate registration with the tracheal-esophageal bifurcation area of the subject and further wherein the retractor has an axial bending stiffness such that a load of about 20 pounds (9 kg) in a transverse direction produces a tip deflection of at least 0.75 inches (1.9 cm) during a tip-deflection test of the holder, which axial bending stiffness is sufficiently large to permit manipulation of the tongue of the subject effective to position the distal end at the bifurcation area, but too small to permit effective use of the apparatus as a laryngoscope blade, wherein the bending stiffness causes the retractor to return to an original position with no external input; and
a fluid dispenser carried near the retractor's distal end.

18. The apparatus of claim 17, wherein the retractor comprises a single member.

* * * * *